United States Patent
Stocks et al.

(10) Patent No.: US 8,485,014 B2
(45) Date of Patent: Jul. 16, 2013

(54) APPARATUS AND METHODS FOR IMBALANCE COMPENSATION

(75) Inventors: Colin Stocks, Crowborough (GB); James Hobby, Crowborough (GB); Martin Lopez, Rotherfield (GB); Chris Edwards, Crowborough (GB)

(73) Assignee: Servomex Group Limited, East Sussex (GB)

( * ) Notice: Subject to any disclaimer, the term of this patent is extended or adjusted under 35 U.S.C. 154(b) by 129 days.

(21) Appl. No.: 13/012,676

(22) Filed: Jan. 24, 2011

(65) Prior Publication Data

US 2012/0035882 A1    Feb. 9, 2012

(30) Foreign Application Priority Data

Feb. 9, 2010    (GB) .................. 1002116.0

(51) Int. Cl.
| | | |
|---|---|---|
| G01N 27/74 | (2006.01) | |
| G01N 27/76 | (2006.01) | |
| G01D 3/06 | (2006.01) | |
| G01L 25/00 | (2006.01) | |
| G01P 21/00 | (2006.01) | |

(52) U.S. Cl.
USPC ............ 73/1.06; 73/1.11; 73/1.14; 73/1.75; 324/201; 324/202; 324/204; 324/225; 702/93

(58) Field of Classification Search
USPC ............ 73/1.06–1.07, 1.11, 1.14, 1.38, 1.75; 324/201–202, 204, 225, 227; 702/87, 93, 702/100, 105
See application file for complete search history.

(56) References Cited

U.S. PATENT DOCUMENTS 2,416,344 A    2/1947  Pauling
2,744,234 A    5/1956  Munday et al.
(Continued)

FOREIGN PATENT DOCUMENTS

| GB | 746778 | 3/1956 |
| GB | 1292724 A | 10/1972 |

(Continued)

OTHER PUBLICATIONS

Examination Report for corresponding European Application No. 11153355.0-2204, dated Jun. 30, 2011.

(Continued)

*Primary Examiner* — Thomas P Noland
(74) *Attorney, Agent, or Firm* — Koppel Patrick Heybl & Philpott

(57) ABSTRACT

Provided are apparatus and methods for compensation of mechanical imbalance in a measurement apparatus, that provides options for increased accuracy and/or less expensive manufacture of a torsion balance. Orientation measurements are taken and an imbalance torque about the torsion spring's axis of rotation is determined, and used to calculate a compensation. The measurement apparatus of one embodiment includes a test body and a set of magnets for generating a first disturbing force on the test body in response to a paramagnetic gas. A conductor element in the magnetic field receives an electrical current that generates a second opposing force to the test body, under feedback control that varies the current until the test body achieves a balanced null position. The control signal required to achieve the fixed null position is measured. Corrections are then made for an imbalance mass by measuring the orientation of the apparatus relative to an acceleration or gravitational field and determining the imbalance torque resulting from the imbalance mass. Use of the invention can improve accuracy or reduce the cost of manufacture of a torsion balance, by enabling compensation for imbalances.

20 Claims, 5 Drawing Sheets

U.S. PATENT DOCUMENTS

| | | | | |
|---|---|---|---|---|
| 3,026,472 A | | 3/1962 | Greene et al. | |
| 3,611,785 A | * | 10/1971 | Hanson | 73/1.75 |
| 3,879,658 A | | 4/1975 | Hummel | |
| 4,300,198 A | * | 11/1981 | Davini | 700/264 |
| 5,896,228 A | * | 4/1999 | Inoue et al. | 359/555 |
| 2007/0144338 A1 | * | 6/2007 | Gerstadt et al. | 89/41.09 |
| 2011/0172817 A1 | * | 7/2011 | Park et al. | 700/245 |
| 2011/0172825 A1 | * | 7/2011 | Lee et al. | 700/261 |
| 2012/0143376 A1 | * | 6/2012 | Seo | 700/261 |

FOREIGN PATENT DOCUMENTS

| | | | | |
|---|---|---|---|---|
| GB | 2196127 A | | 4/1988 | |
| JP | 55065166 A | * | 5/1980 | 324/225 |
| JP | 61162731 A | * | 7/1986 | 73/1.75 |
| JP | 01244971 A | * | 9/1989 | 73/1.11 |
| JP | 03078642 A | * | 4/1991 | 73/1.75 |
| JP | 07093010 A | * | 4/1995 | |

OTHER PUBLICATIONS

B.R. Heckel, et al. "New CP-Violation and Preferred-Frame Tests with Polarized Electrons", Physical Review Letters, vol. 97, 021603, Jul. 14, 2006, pp. 021603-1-021603-4.

E-mail response to UK Intellectual Property Office for Application No. 1002116.0; dated Nov. 3, 2011.

United Kingdom Intellectual Property Office, Examination Report for GB1002116.0; dated Nov. 14, 2011.

Response to UK Examination Report of Nov. 14, 2011 for Application No. 1002116.0,; dated Dec. 14, 2011.

Letter to UK Intellectual Property Office for Application No. 1002116.0; dated Dec. 22, 2011.

"The Magnetic Susceptibility of Nitrogen Dioxide", G. G. Havens, Phys. Rev. vol. 41 (1932) pp. 337-344.

"Highly Accurate Measurement of Oxygen Using a Paramagnetic Gas Sensor", R.P. Kovacich, N. A. Martin, M.G. Clift, C. Stocks, I. Gaskin, J. Hobby, Measurement Science and Technology, vol. 17 (2006), pp. 1579-1585.

United Kingdom Intellectual Property Office, Search Report for Application No. GB1002116.0; dated May 12, 2010.

United Kingdom Intellectual Property Office, Examination Report for Application No. GB1002116.0; dated Aug. 17, 2010.

Response to UK Examination Report for Application No. GB1002116.0; dated Dec. 17, 2010.

United Kingdom Intellectual Property Office, Examination Report for Application No. GB1002116.0; dated Jan. 6, 2011.

Response to UK Examination Report for Application No. GB1002116.0; dated Feb. 9, 2011.

Communication from United Kingdom Intellectual Property Office for GB1002116.0; dated Feb. 17, 2011.

United Kingdom Intellectual Property Office, Notification of Grant: Patent Serial No. GB2477575, for GB1002116.0; dated Jan. 10, 2012.

Certificate of Grant of Patent for Application No. 1002116.0, under Patent No. GB2477575; dated Feb. 8, 2012.

* cited by examiner

APPARATUS AND METHODS FOR IMBALANCE COMPENSATION

This utility patent application claims the benefit of GB1002116.0 filed Feb. 9, 2010 in the United Kingdom.

FIELD OF INVENTION

The present invention relates to a measurement apparatus and provides a method and controller for controlling a measurement apparatus, and a method for calibrating a measurement apparatus. In particular, the invention provides apparatus and methods for compensating mechanical imbalance within a measurement apparatus, such as in a torsion balance of a paramagnetic gas sensor, or an apparatus for measuring a magnetic field.

BACKGROUND

One known example of a measurement apparatus comprises a torsion balance that employs the paramagnetic property of a test gas to measure the partial pressure of the test gas which is present in a measurement chamber. A non-uniform magnetic field is applied across a chamber containing a test body. The test body is held by a suspension filament, acting as a torsion spring, so as to allow the test body to have a single degree of rotational freedom. The non-uniform magnetic field causes a disturbing torque to be applied to the test body in the presence of a paramagnetic gas, and this enables the partial pressure of the paramagnetic gas to be measured. Oxygen is one of a small number of naturally-occurring gases that exhibits paramagnetism, and has a stronger magnetic susceptibility than other gases. Paramagnetic oxygen sensors have been used in a number of industrial and medical applications.

In some examples of systems that measure the partial pressure of oxygen, a test body comprises a pair of hollow glass spheres mounted on a rigid bar, the centre of which is mounted on a fine filament that is held under tension and that is perpendicular to the bar. A strong magnetic field gradient is applied across the assembly such that the force acting on each of the spheres creates a disturbing torque that is opposed by the torsional elasticity of the filament (i.e. the disturbing torque moves the test body until balanced by the torque created by the filament held under tension—the filament behaves as a weak torsion spring). A mechanism of this type is described in U.S. Pat. No. 2,416,344.

The force Fm that acts on a spherical test body in an inhomogeneous magnetic field is proportional to its volume V, the magnetic field strength H and gradient dH/dz and the volume magnetic susceptibility difference between the test body X1 and surrounding sample gas X2 (see "The magnetic susceptibility of nitrogen dioxide", G G Havens, Phys. Rev. vol 41 (1932) pp. 337-344). That is:

$$Fm \propto V^* H^* dH/dz^* (X1-X2)$$

Since the volume magnetic susceptibility of the sample gas is proportional to the sample gas density, the force acting on the test body is proportional to the partial pressure of oxygen. The volume magnetic susceptibility of oxygen at room temperature is $1.9 \times 10^{-6}$ SI units, whereas nitrogen (a typical background gas) is $-6.7 \times 10^{-9}$ SI units. Therefore the force due to oxygen in the gas mixture, even small amounts, is substantially larger than other gas components, hence the excellent selectivity of this measurement principle to oxygen.

The force described above is quite weak, typically a few micro-Newtons with pure oxygen for magnetic field strengths and test body volumes that can be practically achieved. Consequently a very sensitive system is required to measure this force with the resolution typically required for oxygen sensing applications.

The typically preferred arrangement uses a magnetic susceptibility torsion balance inside a sealed cell which includes an inlet to admit the sample gas. The torsion balance comprises a test body filled with a diamagnetic gas (e.g. nitrogen) or an evacuated rigid volume. The body is suspended in a non-uniform magnetic field in the sealed cell, and is typically balanced by initially filling the cell with the same diamagnetic gas that fills the test body. When the cell is subsequently filled with a sample gas containing oxygen, the paramagnetic oxygen gas is attracted to the stronger part of the magnetic field, and the test body rotates. This rotation is detected and used to indicate the oxygen content of the sample gas.

To ensure good linearity and a high level of sensitivity, an electronic optical lever is employed. A light source is reflected from a mirror mounted centrally between the spheres. In early devices, the reflected beam was detected using an optical readout which indicated the degree of displacement. In later developments, the reflected beam is detected using one or more photo detectors, and a controlled electrical current is passed through a conductor wound around the test body substantially perpendicular to the magnetic field in such a way that the torque generated through interaction of the current and the fixed magnetic field acts to oppose the disturbing torque resulting from the paramagnetic gas, to maintain the assembly in a fixed null position. The current required to balance the torsion balance can then be measured in order to determine the disturbing torque resulting from paramagnetic effects, to determine the oxygen content. This modification to the basic mechanism is described in UK patent GB 746,778. Aside from secondary effects, the assembly only permits rotation of the test body around the longitudinal axis of the torsion spring, and inhibits any linear motion of the test body relative to the assembly.

Modern oxygen sensors that require high sensitivity still use the optical lever with refinements (see "Highly accurate measurement of oxygen using a paramagnetic gas sensor", R P Kovacich, N A Martin, M G Clift, C Stocks, I Gaskin, J Hobby, Measurement Science and Technology, vol 17 (2006), pp. 1579-1585). A solid state source (light emitting diode) is used in place of an incandescent one, alongside a pair of photodiodes connected in reverse polarity to provide a zero voltage null position when both photodiodes are equally illuminated, i.e. when the beam spot centre is exactly in between the photodiodes. Using a pair of photodiodes also has the advantage of rejecting common mode errors, such as intensity fluctuations of the light source. This electronic optical lever feedback system gives much improved sensitivity, linearity and stability.

In sensitive measurement systems, such as the example paramagnetic oxygen sensors described above that use a torsion balance, balancing of the mechanical elements is required. Without this balancing, interaction of the imbalance mass and gravity generates forces (an imbalance torque in the case of the example torsion balance described above) that cause erroneous readings.

In particular, if the centre of mass of the rotating test body is not coincident with its axis of rotation (i.e. the suspension filament acting as a torsion spring in the example described above), changes in tilt or orientation of the assembly will change the torque required to maintain the null position of the test body. Thus, when the spheres and associated structures do not have a centre of mass coincident with the torsion spring, balance weights must be added to move the centre of mass to, or close to, the torsion spring. The cost of accurately balancing the test body can be a significant proportion of its manufacturing cost and minor imbalances may remain.

SUMMARY OF INVENTION

A first aspect of the present invention provides a measurement apparatus comprising: a test body that is held by a support enabling rotation of the test body about an axis of rotation; means for generating a first disturbing torque, acting on the test body in a first direction around the axis of rotation, in response to a test stimulus; means for generating a second torque, acting on the test body in a second direction opposite the first direction, in response to a control signal; a controller for varying the control signal until the test body achieves a balanced null position; and means for measuring the control signal required to achieve the balanced null position; further comprising:

means for measuring the orientation of the apparatus relative to an acceleration or gravitational field; and means for calculating, from the measured control signal and measured orientation, a required compensation for the effects of mechanical imbalance and for applying the compensation to a measured control signal to determine a modified control signal required to balance the first disturbing torque.

The present invention can be implemented in a sensitive measurement apparatus, such as apparatus including a torsion balance in which the test body has a single rotational degree of freedom and the first and second torques act around the axis of rotation. The inventors of the present invention have recognized that shortening the time required to achieve a balanced torsion balance, or eliminating the balancing operation entirely, would simplify product manufacture and reduce manufacturing cost. The inventors have provided apparatus and methods that enable mechanical imbalances to be compensated for.

The present invention is advantageous when used to improve accuracy compared with known measurement apparatus, by enabling imbalance compensation. The invention is also advantageous when used to achieve accuracy comparable with known apparatus but at lower manufacturing cost, by virtue of the fact that an ability to compensate for imbalance enables looser manufacturing tolerances.

The orientation can be measured by an inclinometer or an accelerometer, such as a three-axis microelectromechanical system (MEMS) accelerometer. The test stimulus may be entry of a paramagnetic gas into a test chamber of the apparatus. In an embodiment including a torsion balance, the disturbing torque may be applied by a set of magnets that generate a torque on the test body when in the presence of a paramagnetic gas. The measured control signal may be an electrical current that flows within a conductor attached to the test body, or a voltage or other controllable parameter that sets or is representative of the electrical current. The conductor is arranged to lie within the magnetic field, such that the control current generates the second torque on the test body. Alternatively, the control signal may be any other signal that is representative of the controllable second torque.

The measured orientation and measured control signal can be recorded for a plurality of different orientations, using any conventional data recording device and any data recording medium. The calculation of a compensation for mechanical imbalance can be implemented using a new arrangement of known electronic components or using a suitably programmed digital data processing unit, as described in more detail below. The term 'processing unit' will be used herein to refer to any analog or digital data processing component or plurality of components, whether implemented in hardware or software or a combination, for performing the calculation of compensation.

A second aspect of the invention provides a method, for use in a measurement apparatus comprising a test body that is supported to enable rotation about an axis of rotation, means for generating a first disturbing torque, acting on the test body in a first direction around the axis of rotation in response to a test stimulus, means for generating a second torque, acting on the test body in a second direction opposite the first direction in response to a control signal, and a controller for varying the control signal until the test body achieves a balanced null position, wherein the method comprises:

measuring the orientation of the apparatus relative to a gravitational field or acceleration;

measuring the control signal required to achieve the balanced null position;

calculating, from the measured control signal and measured orientation, a required compensation for the effects of mechanical imbalance; and applying the required compensation to a measured control signal to determine the modified control signal required to balance the first disturbing torque.

The calculation of compensation may be performed in the absence of the test stimulus, and then applied to subsequent measurements in the presence of the test stimulus.

The method can include measuring the orientation and control signals for each of a plurality of different orientations of the apparatus and determining a set of parameters characterizing the imbalance moment around the axis of rotation that results from an imbalance mass. A compensation can then be calculated that takes account of the plurality of readings.

A third aspect of the present invention provides a controller for a paramagnetic gas sensor or anemometer system, the system comprising a torsion balance comprising: a test body that is held by a test body support component that enables rotation of the test body about an axis of rotation; means for generating a first disturbing torque, acting on the test body in a first direction around the axis of rotation, in response to a test stimulus; and means for generating a second torque, acting on the test body in a second direction opposite the first direction, in response to a control signal; wherein the controller comprises:

an orientation measurement unit, such as an accelerometer, for measuring the orientation of the sensor system relative to a gravitational field or acceleration;

a control signal measurement unit, such as an ammeter, for measuring a control signal required to achieve a balanced null position of the test body; and a compensation unit, such as a suitably programmed digital signal processing unit, for calculating a required compensation for the effects of mechanical imbalance, based on an orientation measured by the orientation measurement unit and a control signal measured by the control signal measurement unit, and for applying the required compensation to a measured control signal to determine a modified control signal required to balance the first disturbing torque.

The compensation unit may calculate and store compensation coefficients that characterize an imbalance within the apparatus, which coefficients can be applied to a subsequently measured gravitational field and control signal to generate a compensation for the effects of the imbalance in a particular orientation of the apparatus relative to the gravitational field.

A fourth aspect of the invention provides an apparatus comprising:
  a test body held by a test body support component that limits movement of the test body to a single rotational degree of freedom;
  means for generating a first torque, acting on the test body, in a first direction within the single degree of freedom;
  means for generating a second torque, acting on the test body, in a second direction opposing the first direction;
  a controller for applying a control signal to the means for generating the second torque, the controller varying the control signal until the test body is held in a balanced null position;
  means for measuring the control signal that achieves the balanced null position; and
  means for compensating for a mechanical imbalance of the test body, wherein the means for compensating comprises:
    (a) means for measuring the orientation of the apparatus relative to a uniform acceleration or gravitational field, for each of a plurality of different orientations of the apparatus;
    (b) means for recording the measured control signal required to achieve the balanced null position, for each of the plurality of different orientations; and
    (c) means for calculating, from the measured control signals and measured orientations, a required compensation for torsional effects of the mechanical imbalance, and means for applying the compensation to measured control signals.

One embodiment of the present invention provides a measurement apparatus comprising a torsion balance with a test body that is held at a fixed, null position relative to the rest of the apparatus, when in the presence of a disturbing torque. The test body has a single degree of rotational freedom. The disturbing torque arises due to the interaction of the test body with a magnetic field and the interaction between that field and a surrounding sample gas having a different magnetic susceptibility than the test body. The measuring step involves measuring an electrical current in the magnetic field that is required to generate an opposing torque for maintaining or restoring the null position. An example application of this embodiment is in a measurement system that employs the paramagnetic property of a gas such as oxygen (or another paramagnetic gas such as nitrogen dioxide) in a torsion balance to measure the partial pressure of the paramagnetic test gas within the sample gas.

Other applications involve apparatus for measuring a fluid flow or a magnetic field strength. Further aspects and embodiments of the invention will be described in the Detailed Description of Embodiments below.

BRIEF DESCRIPTION OF DRAWINGS

Embodiments of the invention are described below in more detail, by way of example, with reference to the accompanying drawings in which.

DETAILED DESCRIPTION OF EMBODIMENTS

In one embodiment of the present invention, a torsion balance of a measurement apparatus includes a test body that has a disturbing torque applied to it as well as a controlled opposing torque for balancing the disturbing torque. Measuring the control signal (e.g. the electrical current) that generates the opposing torque provides an effective measurement of the stimulus that caused the disturbing torque. In a particular example, measuring an input current required to balance the effects of a magnetic field applied across a chamber containing a sample gas provides an effective measurement of the partial pressure of a paramagnetic test gas within the chamber. Components are provided to enable compensation for mechanical imbalance of the test body. An orientation detector such as an accelerometer or inclinometer is used to determine the orientation of the test body relative to the earth's gravitational field or an applied acceleration, and this can be carried out for a plurality of different orientations of the apparatus. For each of the plurality of orientations, measurements are taken of a parameter of the apparatus that is representative of the opposing torque required to balance the disturbing torque and a torque resulting from mechanical imbalance, and these measurements are used to determine a required compensation for the imbalance torque resulting from an imbalance mass. Techniques are employed, as described below, that allow compensation values to be determined regardless of the orientation of the accelerometer or inclinometer relative to the test body, as long as this remains fixed.

Figure 1:
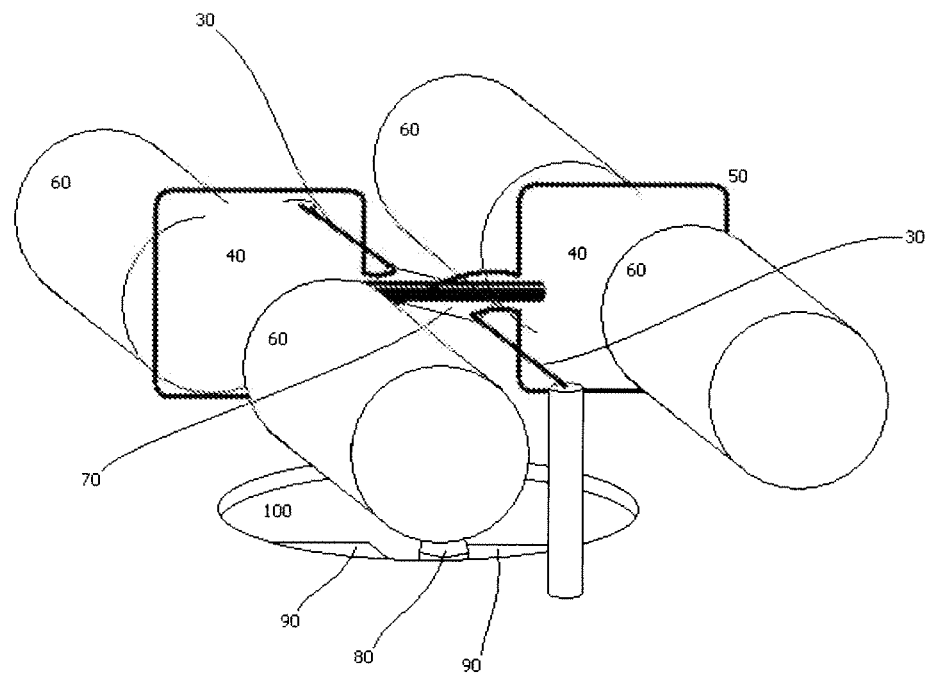
FIG. 1 is a schematic representation of a paramagnetic measurement apparatus including a torsion balance, in which the present invention can be implemented.

FIG. 1 schematically illustrates a torsion balance 10 of a measurement apparatus that can employ the invention. The torsion balance comprises a test body 20 suspended by a filament 30 that provides an axis of rotation of the test body. The test body has a pair of hollow glass spheres 40 containing a diamagnetic gas, the spheres being held at a fixed separation by a rigid bar. In this embodiment, the filament 30 forms part of an electrical conductor 50 that is also coiled around each of the spheres. A non-uniform magnetic field is created in the vicinity of each sphere by a set of paired magnets 60. Where the filament joins a central point of the rigid bar, a mirror 70 is located for use in detecting rotational movement of the test body. A light source 80 shines a beam of light through a window 100 onto the mirror 70, and light reflected from the mirror can be detected by one or more photo detectors 90 located on a printed circuit board. The test body is held in a gas-sealed cell, which has an inlet for receiving the sample gas. When the sample gas includes oxygen, the paramagnetic oxygen is attracted by the magnetic field, applying a disturbing torque to the test body against the torsional resistance of the suspension filament 30. Rotation of the test body has a measurable effect on the beam of light reflected from the mirror.

By passing an electrical current through the electrical conductor coil 50 of the test body, the resulting magnetic field effect can generate an opposing torque. The electrical current supplied to the conductor 50 is responsive to a control signal that is generated in response to a signal from the photo detectors, to achieve an electromagnetic field effect that balances the torques at the null position of the torsion balance.

Apparatus such as shown in FIG. 1 would normally rely on careful machining of the components of the test body to minimize any mechanical imbalance in the system, but also the application of small balance masses to move the centre of mass of the test body as close as possible to the suspension filament 30. However, this machining and balancing is time consuming and expensive.

The present invention avoids the need to mechanically balance out such an imbalance mass, by determining the effects of the imbalance mass, and calculating and applying a compensation for these effects. An effective imbalance mass 22 of the test body 20 can be represented schematically as in FIG. 2, and can be modelled as a point mass for the purposes of analysis.

A controller includes an orientation measurement unit 200, a control signal measurement unit for measuring the current supplied to the electrical conductor coil, a data storage unit for storing data representing an imbalance moment of the test body around the axis of rotation, and a compensation unit for calculating and applying a required compensation to the measured control signals, based on the stored data, the measured orientation and the measured control signals. A micro-machined accelerometer 200 is used to detect the orientation of the measurement apparatus relative to the earth's gravitational field, or to detect an applied acceleration, in one, two, or three orthogonal axes. In the case where three axes are measured, the magnitude and direction of the gravitational field or uniform acceleration can be completely specified. The accelerometer in this embodiment is a microelectromechanical system (MEMS) accelerometer, soldered onto the printed circuit board. A three-axis accelerometer is preferred for the present invention. However, other accelerometers or inclinometers may be used. An accelerometer can be as simple as a micro-machined cantilever beam with a proof mass that deflects as the apparatus changes orientation, means for measuring the deflection and a signal output representing the orientation. The deflection measurement device can be an optical device, an analogue device using capacitance, or a digital device.

Figure 2:
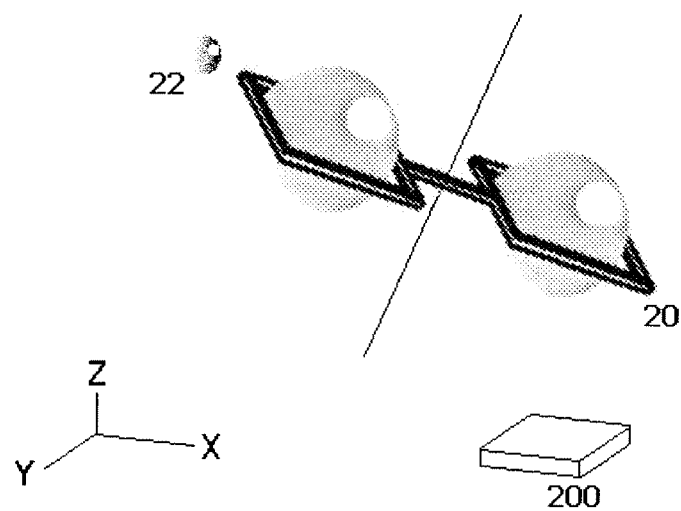
FIG. 2 is a schematic representation of a test body, an imbalance mass, and an orientation sensor.

The test body 20 is depicted in FIG. 2 at an arbitrary orientation relative to the accelerometer and its frame of reference (illustrated with X, Y, and Z axes). The orientation of the test body 20 relative to accelerometer 200 must remained fixed. It is not necessary to know the orientation of the accelerometer relative to any other part of the system, only that the position of the accelerometer remains fixed relative to the test body. An accelerometer with one, two or three orthogonal measurement axes may be used, but the correction determined will apply only in the number of axes measured. For comprehensive imbalance compensation a three-axis accelerometer must be employed. A general three-axis analysis is given below. In assemblies using fewer accelerometer axes, the relevant terms can be omitted from the computation expressions.

If the position and mass of the imbalance is exactly known, and the nulling torque, if any, required in the absence of imbalance mass is also exactly known, accelerometer measurements can be used to compensate for the error without requiring a characterisation operation to determine the imbalance moment. For example, the position and mass of the imbalance may be known from testing torsion balances at a manufacturing facility. If the same imperfection is repeated, data representing the imbalance such as compensation coefficients can be stored and used for a batch of torsion balances.

However, in most cases, these parameters will not be known in advance, and characterisation of the individual apparatus is required. This characterization operation can be carried out at a first time and location, determining system parameters and storing a set of coefficients representing those parameters. The characterizing operation can involve positioning the apparatus in various orientations and determining the particular controllable input current, supplied to the electrical conductor that is attached to the test body, required to balance the torsion balance at each orientation. A set of coefficients representing the imbalance can then be calculated and stored in a non-volatile memory. Thereafter, and potentially when the apparatus is at a different location and orientation, the coefficients can be applied to measured data to determine a required compensation.

The compensation can be inexpensively and accurately effected using digital electronics to calculate the compensation terms, but can also be effected using analogue computing techniques to generate a correction value, which can be applied as a voltage or current in electronic systems, or using other continuously variable media or forces where relevant.

Analysis of the system uses the accelerometer's frame of reference, in which the position of the nulled test body, and all other elements of the assembly, are static. Only the external gravitational field or uniform acceleration have variable magnitude and direction, which can be directly measured using the accelerometer.

Figure 3:
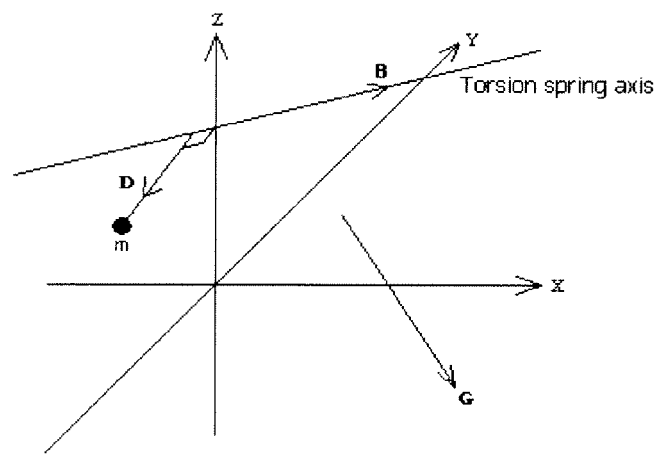
FIG. 3 represents three vectors against the X, Y and Z reference axes.

FIG. 3 shows a simplified diagram of the vectors that represent the system, against X, Y and Z reference axes.

The bold characters, B, D, and G in FIG. 3 represent the vectors. B is the vector designating the direction of the torsion spring, D is a vector perpendicular to B that defines the shortest distance of the imbalance point mass, m, from the torsion spring, and G defines the gravitational field vector acting on the test body or the uniform acceleration it is subjected to (relative to the accelerometer's frame of reference).

The frame of reference of the system is determined by the accelerometer axes. B and D define a plane in which the imbalance mass, m, lies. If B' and D' represent unit vectors parallel to B and D, respectively, then the vector product of B' and D' represents the unit vector normal to the plane defined by B and D.

The component of G acting perpendicular to the plane, and therefore creating the imbalance moment about the torsion spring, is determined by calculating the scalar product of G and the vector product of B' and D'. Finally, the imbalance moment is determined by multiplying the result of the last calculation by the mass, m, and the shortest distance, |D|, between the suspension filament and the point mass.

Mathematically, $$I = m|D|G \cdot (B' \times D') \quad \text{equation 1}$$

where I is the imbalance moment.

Where B, D and m are known, G is measured by the accelerometer, and the imbalance compensation is calculated directly. However, there will be mechanisms for which these values are not known and cannot readily be determined. An embodiment of the present invention that is described below includes a mechanism for deriving a compensation vector through a small number of measurements.

In the absence of the measured substance or field, a torque will be required to maintain the null position of the test body. In a perfectly balanced system, this null restoring torque will be determined solely by the torque created by the torsion spring when the test body is in the null position. In most practical systems, the null position restoring torque will not be zero, so the derivation of unknown characteristics must include determination of the null torque, $T_{null}$, which is the torque required to maintain the null position in the absence of imbalance and in the absence of a measured substance or field.

An imbalance vector, I, includes three terms, corresponding to the three coordinate axes. Each of these terms, plus the null torque, must be determined. To accomplish this, the measurement assembly is manipulated to adopt four different and distinct orientations. In each orientation, the gravitational field vector, G, and the restoring torque, T (or restoring current, A, which is representative of T) are recorded. The measured values are then used to calculate $T_{null}$ and the three terms of the imbalance vector. These calculated terms are stored and can be applied to subsequent measurements to compensate for the imbalance. The manipulation can be performed as part of a calibration operation when the apparatus is positioned for use, but can also be carried out at a different time and location. It is not necessary to repeat this manipulation for calibration purposes before each use of the apparatus, even if the orientation changes.

Figure 7:
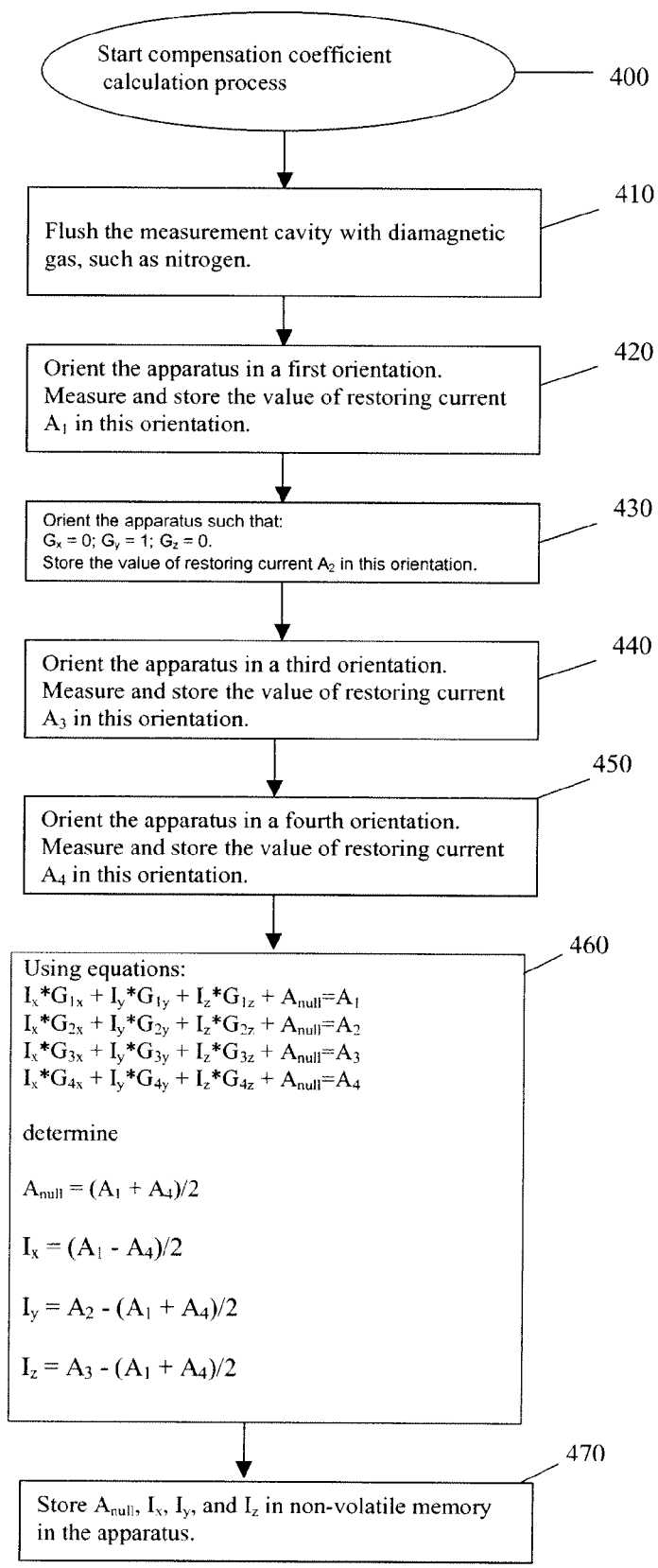
FIG. 7 is a schematic flow diagram showing a sequence of steps for calculating a required compensation for the effects of imbalance.

A paramagnetic oxygen measuring apparatus, which is capable of rotation in three axes for calibration purposes, can be compensated for mechanical imbalance using the operating sequence shown in FIG. 7. When the measuring apparatus is ready to be characterised, it can be mounted on a test rig that includes a tiltable platform and the compensation coefficient calculation procedure can be started 400. The measurement cavity is initially flushed 410 with a diamagnetic gas, so that the characterisation is performed in the absence of paramagnetic gas, such that the test body and surrounding gas will experience the same diamagnetic effect. The apparatus is then positioned 420 in a first orientation, for example an orientation in which the components of a unit vector in a direction parallel to the gravitational field vector ($G_X$, $G_Y$, $G_Z$) are (1,0,0). An electrical current is passed through the electrical conductor coil that surrounds the test body and is varied until the torque it generates balances the combined effect of the disturbing torque and the null torque. The current $A_1$ that achieves this balance is then recorded with the orientation data. The apparatus is then reoriented 430 into a second orientation—for example such that the unit vector parallel to ($G_X$, $G_Y$, $G_Z$) is (0,1,0)—and the restoring current $A_2$ is measured and recorded with the orientation data. Another reorientation is performed 440, followed by measurement of orientation and a restoring current $A_3$, and recording of this data, for the third orientation—for example such that the unit vector parallel to ($G_X$, $G_Y$, $G_Z$) is (0,0,1). A further reorientation 450 is carried out, into a fourth orientation, such that the unit vector parallel to ($G_X$, $G_Y$, $G_Z$) is (-1,0,0), and a further restoring current $A_4$ is measured and recorded with the respective orientation data.

The specific calibration points shown in FIG. 7, in which the gravity vector terms for two of the three axes are reduced to zero at each measurement orientation, simplify the mathematics required to determine the compensation vector and null position current. Note that in the simple example above, ½, ($A_1+A_4$) will give $A_{null}$. Note also that $A_{null}=kT_{null}$, where k is a constant, $A_{null}$ is the null position restoring current, and $T_{null}$ is the null position restoring torque, in the absence of any imbalance. Similarly, $A_1=kT_1$, $A_2=kT_2$, $A_3=kT_3$, and $A_4=kT_4$, The specific calibration points mentioned above with reference to FIG. 7 are merely exemplary, and other orientations can be used. In particular, it is not essential to change orientation through a full 90° before new measurements are taken, and smaller changes can be used. The orientation and reorientation of the apparatus (described above) is preferably fully automated but could be performed under manual control.

As shown in step 460 and step 470, a data processing unit then solves a set of simultaneous equations to determine components of an imbalance vector, $I_X$, $I_Y$ and $I_Z$. These vector components can be stored and subsequently multiplied by a gravitational field vector G to determine the current A required to balance the effects of mechanical imbalance.

Thus, the data captured in the four different orientations will, when suitably arranged, form a set of four simultaneous equations that can be solved to find the restoring torque (or current) in the absence of imbalance or measured substance or field, and the three independent terms in I.

Mathematically, solve:

$$I_x \cdot G_{1x} + I_y \cdot G_{1y} + I_z \cdot G_{1z} + T_{null} = T_1 \qquad \text{equation 2}$$

$$I_x \cdot G_{2x} + I_y \cdot G_{2y} + I_z \cdot G_{2z} + T_{null} = T_2 \qquad \text{equation 3}$$

$$I_x \cdot G_{3x} + I_y \cdot G_{3y} + I_z \cdot G_{3z} + T_{null} = T_3 \qquad \text{equation 4}$$

$$I_x \cdot G_{4x} + I_y \cdot G_{4y} + I_z \cdot G_{4z} + T_{null} = T_4 \qquad \text{equation 5}$$

where $I_x$, $I_y$, and $I_z$ are the components of unknown imbalance vector I, $G_{nx}$, $G_{ny}$, and $G_{nz}$ are the components of measured vector G in the four different orientations (with n taking values 1, 2, 3, or 4), and $T_1$, $T_2$, $T_3$, and $T_4$ are the restoring torques in the four different orientations. The restoring torques can be determined by measuring $A_1$, $A_2$, $A_3$ and $A_4$, which are the measured restoring currents generating $T_1$, $T_2$, $T_3$, and $T_4$, respectively. For the purposes of our calculations, we can disregard the constant k and the different units of A and T to determine the coefficients of I that correspond to the effects of the imbalance, since the system according to this embodiment of the invention enables us to evaluate either a torque, an electrical current that generates that torque, or a voltage or control signal that generates that current, for example. We can then apply a suitable multiplying factor according to which of these proportional parameters we have decided to use in our calculations. Given that the restoring current A is proportional to the restoring torque T, we can mathematically solve:

$$I_x \cdot G_{1x} + I_y \cdot G_{1y} + I_z \cdot G_{1z} + A_{null} = A_1 \qquad \text{equation 6}$$

$$I_x \cdot G_{2x} + I_y \cdot G_{2y} + I_z \cdot G_{2z} + A_{null} = A_2 \qquad \text{equation 7}$$

$$I_x \cdot G_{3x} + I_y \cdot G_{3y} + I_z \cdot G_{3z} + A_{null} = A_3 \qquad \text{equation 8}$$

$$I_x \cdot G_{4x} + I_y \cdot G_{4y} + I_z \cdot G_{4z} + A_{null} = A_4 \qquad \text{equation 9}$$

Many techniques are available for the solution of simultaneous equations, and most are applicable. For example, algebraic manipulation of the expressions gives the analytical results shown in equations 11, 12, 13 and 14 in Appendix 1 of this specification (which use torque instead of current in that example). The numerical values obtained from measurement of the system can be inserted into the expressions in Appendix 1.

For the well conditioned and limited set of equations involved, the analytical solution has been found to be very effective and simple to implement. However, a numerical solution can be determined using, for example but not limited to, Gauss-Jordan Elimination (with or without pivoting, but with only four equations pivoting has been found to be unnecessary), LU Decomposition, or Singular Value Decomposition.

Subsequently, I is used in conjunction with G to calculate the component of torque due to imbalance, and this can then be used to numerically correct for the error, or a compensating torque can be applied directly.

Mathematically, $$T_{imbalance} = I \cdot G \quad \text{equation 10}$$

where $T_{imbalance}$ is the torque due to mechanical imbalance of the test body at the time of measurement of G.

Note that $I = m|D|(B' \times D')$

Figure 4:
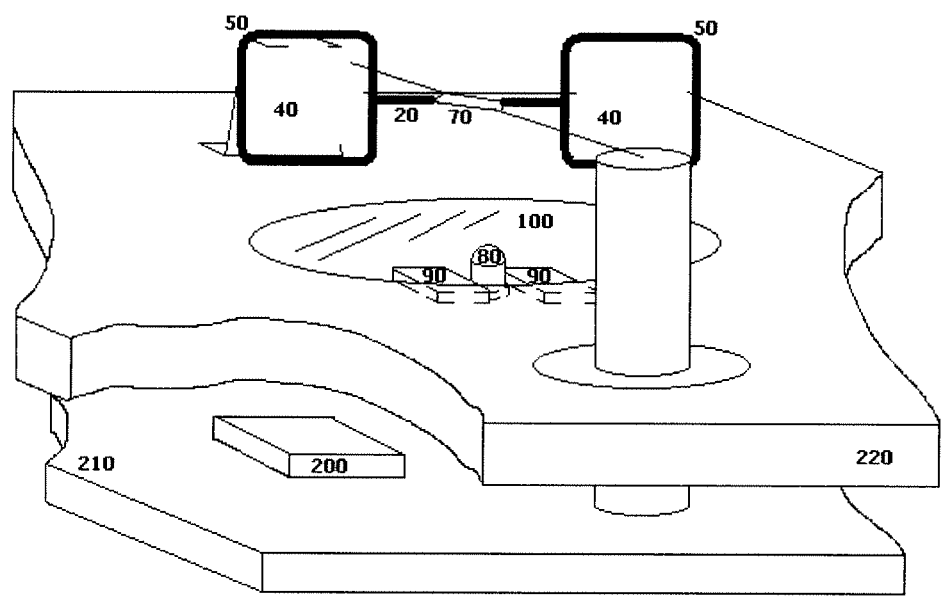
FIG. 4 is a schematic representation of a measurement apparatus according to an embodiment of the invention.

FIG. 4 shows an oxygen concentration measurement system employing a test body that comprises two nitrogen filled spheres placed in a non-uniform magnetic field, and that is maintained in a null position by passing a current through a coil wound around the spheres. A three-axis accelerometer 200 is mounted on a circuit board 210 that is rigidly connected to the system. Item 20 identifies the test body comprising the spheres 40 and coil 50, item 200 is the three-axis accelerometer soldered to printed circuit board item 210. The circuit board is, in turn, attached through rigid mechanical fixtures and solder joints to mounting plate item 220. The mounting plate includes a clear window, item 100, that permits a light source 80 to illuminate a mirror 70 mounted in the centre of the test body. Light reflected off the mirror illuminates photocells 90, and an electronic circuit creates a restoring current that flows through the coil around the test body spheres, thereby maintaining the test body in a fixed orientation relative to the mounting plate and thus also to the printed circuit board and accelerometer.

The volume containing the test body can be filled with a gas under test. Should the gas contain oxygen, the oxygen is attracted to the area of highest magnetic field strength, and attempts to displace the nitrogen filled spheres. The restoring current required to counteract the resulting torque is proportional to the partial pressure of the oxygen in the test volume.

During a characterisation phase, electronic circuits within the instrument measure the restoring current and the gravitational field vector corresponding to the current orientation (or an applied acceleration) in all three axes in each of four different positions. This characterisation is performed following assembly of the unit, but prior to use as an oxygen sensor. Imbalance compensation values are calculated from the data acquired and are stored in a non-volatile electronic memory included in the unit.

Figure 5:
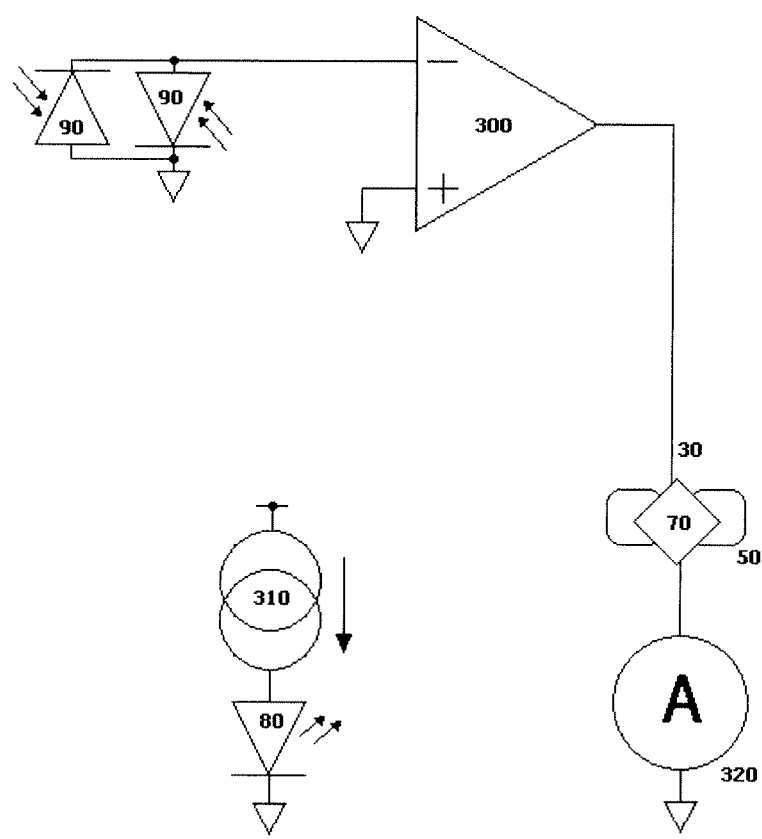
FIG. 5 is a schematic representation of an electrical control circuit that is used in the apparatus depicted in FIG. 4.

FIG. 5 shows the schematic of an electrical circuit used to maintain the test body in a null position in a preferred embodiment of the oxygen measuring system. Photocells 90 are connected in anti-parallel such that they produce no current when they are equally illuminated. Illumination is provided by LED 80 driven by current source 310. Light from LED 80 reflects from mirror 70, mounted on the test body, such that in the null position photocells 90 both receive the same amount of illumination. Any deviation from the null position is determined through use of an operational amplifier 300, and the amplified error causes current to flow through the torsion element 30 and restoring current coils 50. The restoring current required to maintain the test body in the null position is detected by ammeter 320.

The schematic of FIG. 5 depicts a simple and low cost mechanism, but other methods can be used including, but not limited to: direct digitisation of the photocell current with the use of a digital signal processor implementing an algorithm to control a variable current source that maintains the test body null position; or manual adjustment of a variable current source to maintain the test body null position.

Figure 6:
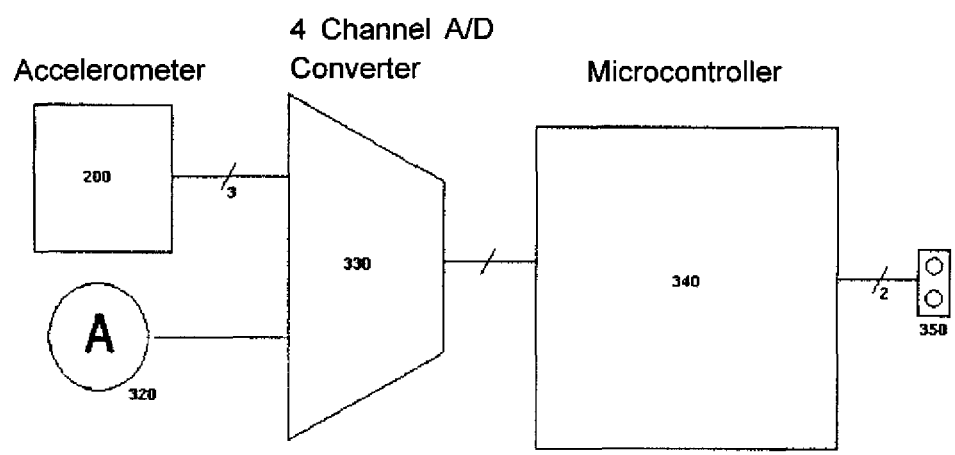
FIG. 6 is a simplified electrical schematic of a compensation circuit that is used in conjunction with the apparatus depicted in FIG. 4 and the electrical circuit depicted in FIG. 5.

FIG. 6 shows a simplified schematic of a measurement and compensation system used in a preferred embodiment of the imbalance compensation system used for oxygen measurement. Analogue signals from a calibrated three axis accelerometer 200 and a restoring-current-measuring ammeter 320 are digitised by four channel analogue-to-digital converter 330. Microcontroller 340 incorporates a non-volatile memory to store the compensation coefficients and it applies the formulae shown in equations 11, 12, 13, and 14 in Appendix 1 to calculate a compensation that cancels out the imbalance errors from the oxygen measurement reading taken from ammeter 320. Media interface 350 allows connection to external equipment for measurement reporting.

Appendix 1

$$d_1 = G_{1x} \cdot \begin{bmatrix} (G_{3z} - G_{4z}) \cdot G_{2y} + (G_{4z} - G_{2z}) \cdot \\ G_{3y} + (G_{2z} - G_{3z}) \cdot G_{4y} \end{bmatrix} \quad \text{Equation 11}$$

$$d_2 = G_{2x} \cdot \begin{bmatrix} (G_{4z} - G_{3z}) \cdot G_{1y} + (G_{1z} - G_{4z}) \cdot \\ G_{3y} + (G_{3z} - G_{1z}) \cdot G_{4y} \end{bmatrix}$$

$$d_3 = G_{3x} \cdot \begin{bmatrix} (G_{2z} - G_{4z}) \cdot G_{1y} + (G_{4z} - G_{1z}) \cdot \\ G_{2y} + (G_{1z} - G_{2z}) \cdot G_{4y} \end{bmatrix}$$

$$d_4 = G_{4x} \cdot \begin{bmatrix} (G_{3z} - G_{2z}) \cdot G_{1y} + (G_{1z} - G_{3z}) \cdot \\ G_{2y} + (G_{2z} - G_{1z}) \cdot G_{3y} \end{bmatrix}$$

$$D = d_1 + d_2 + d_3 + d_4$$

$$n_1 = T_1 \cdot \begin{bmatrix} (G_{3z} - G_{4z}) \cdot G_{2y} + (G_{4z} - G_{2z}) \cdot \\ G_{3y} + (G_{2z} - G_{3z}) \cdot G_{4y} \end{bmatrix}$$

$$n_2 = T_2 \cdot \begin{bmatrix} (G_{4z} - G_{3z}) \cdot G_{1y} + (G_{1z} - G_{4z}) \cdot \\ G_{3y} + (G_{3z} - G_{1z}) \cdot G_{4y} \end{bmatrix}$$

$$n_3 = T_3 \cdot \begin{bmatrix} (G_{2z} - G_{4z}) \cdot G_{1y} + (G_{4z} - G_{1z}) \cdot \\ G_{2y} + (G_{1z} - G_{2z}) \cdot G_{4y} \end{bmatrix}$$

$$n_4 = T_4 \cdot \begin{bmatrix} (G_{3z} - G_{2z}) \cdot G_{1y} + (G_{1z} - G_{3z}) \cdot \\ G_{2y} + (G_{2z} - G_{1z}) \cdot G_{3y} \end{bmatrix}$$

$$I_x = \frac{n_1 + n_2 + n_3 + n_4}{D}$$

$$n_5 = T_1 \cdot \begin{bmatrix} (G_{4z} - G_{3z}) \cdot G_{2x} + (G_{2z} - G_{4z}) \cdot \\ G_{3x} + (G_{3z} - G_{2z}) \cdot G_{4x} \end{bmatrix} \quad \text{Equation 12}$$

$$n_6 = T_2 \cdot \begin{bmatrix} (G_{3z} - G_{4z}) \cdot G_{1x} + (G_{4z} - G_{1z}) \cdot \\ G_{3x} + (G_{1z} - G_{3z}) \cdot G_{4x} \end{bmatrix}$$

$$n_7 = T_3 \cdot \begin{bmatrix} (G_{4z} - G_{2z}) \cdot G_{1x} + (G_{1z} - G_{4z}) \cdot \\ G_{2x} + (G_{2z} - G_{1z}) \cdot G_{4x} \end{bmatrix}$$

$$n_8 = T_4 \cdot \begin{bmatrix} (G_{2z} - G_{3z}) \cdot G_{1x} + (G_{3z} - G_{1z}) \cdot \\ G_{2x} + (G_{1z} - G_{2z}) \cdot G_{3x} \end{bmatrix}$$

$$I_y = \frac{n_5 + n_6 + n_7 + n_8}{D}$$

$$n_9 = T_1 \cdot \begin{bmatrix} (G_{3y} - G_{4y}) \cdot G_{2x} + (G_{4y} - G_{2y}) \cdot \\ G_{3x} + (G_{2y} - G_{3y}) \cdot G_{4x} \end{bmatrix} \quad \text{Equation 13}$$

$$n_{10} = T_2 \cdot \begin{bmatrix} (G_{4y} - G_{3y}) \cdot G_{1x} + (G_{1y} - G_{4y}) \cdot \\ G_{3x} + (G_{3y} - G_{1y}) \cdot G_{4x} \end{bmatrix}$$

$$n_{11} = T_3 \cdot \begin{bmatrix} (G_{2y} - G_{4y}) \cdot G_{1x} + (G_{4y} - G_{1y}) \cdot \\ G_{2x} + (G_{1y} - G_{2y}) \cdot G_{4x} \end{bmatrix}$$

$$n_{12} = T_4 \cdot \begin{bmatrix} (G_{3y} - G_{2y}) \cdot G_{1x} + (G_{1y} - G_{3y}) \cdot \\ G_{2x} + (G_{2y} - G_{1y}) \cdot G_{3x} \end{bmatrix}$$

$$I_z = \frac{n_9 + n_{10} + n_{11} + n_{12}}{D}$$

$$n_{13} = T_1 \cdot \begin{bmatrix} (G_{3z} \cdot G_{4y} - G_{3y} \cdot G_{4z}) \cdot G_{2x} + \\ (G_{4z} \cdot G_{2y} - G_{4y} \cdot G_{2z}) \cdot G_{3x} + \\ (G_{3y} \cdot G_{2z} - G_{3z} \cdot G_{2y}) \cdot G_{4x} \end{bmatrix} \quad \text{Equation 14}$$

$$n_{14} = T_2 \cdot \begin{bmatrix} (G_{4z} \cdot G_{3y} - G_{4y} \cdot G_{3z}) \cdot G_{1x} + \\ (G_{1z} \cdot G_{4y} - G_{4z} \cdot G_{1y}) \cdot G_{3x} + \\ (G_{3z} \cdot G_{1y} - G_{1z} \cdot G_{3y}) \cdot G_{4x} \end{bmatrix}$$

-continued $$n_{15} = T_3 \cdot \begin{bmatrix} (G_{4y} \cdot G_{2z} - G_{4z} \cdot G_{2y}) \cdot G_{1x} + \\ (G_{4z} \cdot G_{1y} - G_{4y} \cdot G_{1z}) \cdot G_{2x} + \\ (G_{1z} \cdot G_{2y} - G_{1y} \cdot G_{2z}) \cdot G_{4x} \end{bmatrix}$$

$$n_{16} = T_4 \cdot \begin{bmatrix} (G_{3z} \cdot G_{2y} - G_{3y} \cdot G_{2z}) \cdot G_{1x} + \\ (G_{3y} \cdot G_{1z} - G_{3z} \cdot G_{1y}) \cdot G_{2x} + \\ (G_{1y} \cdot G_{2z} - G_{1z} \cdot G_{2y}) \cdot G_{3x} \end{bmatrix}$$

$$T_{null} = \frac{n_{13} + n_{14} + n_{15} + n_{16}}{D}$$

The invention claimed is:

1. A paramagnetic gas sensor apparatus comprising:
a test body held by a support enabling rotation of the test body about an axis of rotation;
a set of magnets for generating a magnetic field that generates a first disturbing torque, acting on the test body in a first direction about the axis of rotation, in response to a test stimulus;
an electrical conductor element for location in the magnetic field, for generating a second torque when an electrical current flows within the electrical conductor element, acting on the test body in a second direction opposite the first direction, in response to a control signal;
a controller for varying the control signal until the test body achieves a balanced null position; and
a signal measurement unit for measuring the control signal required to achieve the balanced null position;
further comprising:
an orientation detector for measuring the orientation of the apparatus relative to an acceleration or gravitational field;
a processing unit to calculate, from the measured control signal and measured orientation, a required compensation for the effects of mechanical imbalance; and
means for applying the compensation to a measured control signal to determine a modified control signal required to balance the first disturbing torque.

2. A paramagnetic gas sensor apparatus according to claim 1, wherein the orientation detector is an accelerometer.

3. A paramagnetic gas sensor apparatus according to claim 2, wherein the accelerometer is a three-axis accelerometer.

4. A paramagnetic gas sensor apparatus according to claim 2, wherein the accelerometer is a microelectromechanical system (MEMS) accelerometer.

5. A paramagnetic gas sensor apparatus according to claim 1, wherein the orientation detector is an inclinometer.

6. A paramagnetic gas sensor apparatus according to claim 1, further comprising:
a position control apparatus for positioning the apparatus in each of a plurality of different orientations; and
a data recording medium for recording the measured control signal and measured orientation for each of the plurality of different orientations, wherein the processing unit is arranged to access the data recording medium.

7. A paramagnetic gas sensor apparatus according to claim 1, comprising a torsion balance in which the test body is supported by a suspension filament that is fixed at each end, the suspension filament defining the axis of rotation for the test body.

8. A paramagnetic gas sensor apparatus according to claim 7, wherein the processing unit determines an imbalance vector representing the imbalance moment about the axis of rotation defined by the suspension filament, and calculates a compensation corresponding to the control signal required to generate a torque to balance the torque resulting from the imbalance moment, which control signal is required to achieve the balanced null position in the absence of the test stimulus.

9. A paramagnetic as sensor apparatus according to claim 1, comprising:
a body defining a test chamber for containing a paramagnetic test gas having a different magnetic susceptibility from the test body, a mounting support for supporting the test body within the test chamber, and wherein the set of magnets is arranged to generate a magnetic field across the test chamber, thereby to generate a torque on the test body due to the different magnetic susceptibility of the test body compared with the test gas.

10. A paramagnetic gas sensor apparatus according to claim 9, wherein the electrical conductor element is arranged between the magnets and is connected to an electrical supply to generate an opposing torque on the test body resulting from the interaction between the magnetic field of the magnets and the electrical conductor.

11. A paramagnetic gas sensor apparatus according to claim 1, including a light source, wherein the controller comprises an electrical feedback control circuit including one or more photo detectors, the photo detectors being arranged to detect light from the light source after the light is reflected from a reflective surface attached to the test body.

12. A paramagnetic gas sensor apparatus according to claim 11, wherein the test body is held within a test chamber and the test stimulus is insertion into the test chamber of a paramagnetic gas.

13. A paramagnetic gas sensor apparatus according to claim 1, wherein the test stimulus is insertion of a test substance.

14. A paramagnetic gas sensor apparatus according to claim 1, wherein the test stimulus is a change in a magnetic field.

15. A paramagnetic gas sensor apparatus according to claim 1, wherein the test stimulus is a field to be measured that generates a torque on the test body.

16. A paramagnetic gas sensor apparatus comprising:
a test body held by a support enabling rotation of the test body about an axis of rotation;
means for generating a first disturbing torque, acting on the test body in a first direction about the axis of rotation, in response to a test stimulus;
means for generating a second torque, acting on the test body in a second direction opposite the first direction, in response to a control signal;
a controller for varying the control signal until the test body achieves a balanced null position; and
a signal measurement unit for measuring the control signal required to achieve the balanced null position;
further comprising:
an orientation detector for measuring the orientation of the apparatus relative to an acceleration or gravitational field;
a processing unit that is programmed to calculate, from the measured control signal and measured orientation, a required compensation for the effects of mechanical imbalance; and
means for applying the compensation to a measured control signal to determine a modified control signal required to balance the first disturbing torque.

17. A paramagnetic gas sensor apparatus according to claim 16, wherein the test stimulus is a torque generated due to the flow of a fluid across the test body.

18. A method, for use in a paramagnetic gas sensor apparatus comprising a test body that is held by a support enabling rotation of the test body about an axis of rotation, means for generating a first disturbing torque, acting on the test body in a first direction around the axis of rotation in response to a test stimulus, means for generating a second torque, acting on the test body in a second direction opposite the first direction in response to a control signal, and a controller for varying the control signal until the test body achieves a balanced null position, wherein the method comprises:

measuring the orientation of the apparatus relative to a gravitational field or an acceleration;

measuring the control signal required to achieve the balanced null position;

calculating, from the measured control signal and measured orientation, a required compensation for the effects of mechanical imbalance; and applying the required compensation to a measured control signal to determine a modified control signal required to balance the first disturbing torque.

19. A method according to claim 18, further comprising:

measuring the orientation and control signals for each of a plurality of different orientations of the apparatus; and wherein the calculation of a compensation is carried out to take account of the plurality of measurements.

20. A controller for a paramagnetic gas sensor system, the system comprising a torsion balance comprising:

a test body that is held by a test body support component that enables rotation of the test body about an axis of rotation;

a set of magnets for generating a magnetic field for generating a first disturbing torque, acting on the test body in a first direction around the axis of rotation, in response to a test stimulus; and an electrical conductor for location within the magnetic field for generating a second torque when an electrical current flows through the electrical conductor, acting on the test body in a second direction opposite the first direction, in response to a control signal;

wherein the controller comprises:

an orientation measurement unit for measuring the orientation of the sensor system relative to a gravitational field;

a control signal measurement unit for measuring a control signal required to achieve a balanced null position of the test body; and a compensation unit for calculating a required compensation for the effects of mechanical imbalance, based on an orientation measured by the orientation measurement unit and a control signal measured by the control signal measurement unit, and for applying the required compensation to a measured control signal to determine a modified control signal required to balance the first disturbing torque.

\* \* \* \* \*